United States Patent
Nahar et al.

(10) Patent No.: US 6,498,016 B1
(45) Date of Patent: Dec. 24, 2002

(54) RAPID METHOD FOR ENZYME-LINKED IMMUNOSORBENT ASSAY

(75) Inventors: Pradip Nahar, Delhi (IN); Utpal Bora, Delhi (IN); Gainda Lal Sharma, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/652,379

(22) Filed: Aug. 31, 2000

(30) Foreign Application Priority Data

Aug. 16, 2000 (IN) .................................. PCT/N00/00075

(51) Int. Cl.$^7$ ................... G01N 33/48; G01N 33/5433; C12M 1/02
(52) U.S. Cl. ................... 435/7.92; 435/1.1; 435/1.3; 435/6; 435/40.5; 435/40.52; 435/176; 435/325; 436/172; 422/20; 422/52; 422/78; 422/100; 427/2.13; 427/543; 250/250; 250/361; 250/459.1; 219/687
(58) Field of Search ........................... 435/1.3, 6, 40.5, 435/1.1, 40.52, 325, 176, 792; 436/172; 422/20, 52, 100, 78; 427/2.13, 543; 250/250, 361, 459.1; 219/687

(56) References Cited

U.S. PATENT DOCUMENTS

| | | | | |
|---|---|---|---|---|
| 4,948,975 A | * | 8/1990 | Erwin et al. ................. | 250/361 |
| 5,304,766 A | | 4/1994 | Baudet et al. ............... | 219/687 |
| 5,455,008 A | | 10/1995 | Earley et al. ................ | 422/100 |
| 6,291,180 B1 | * | 9/2001 | Chu ............................... | 435/6 |

FOREIGN PATENT DOCUMENTS

| | | | | |
|---|---|---|---|---|
| EP | 0604970 | | 7/1994 | |
| JP | 08082627 | | 3/1996 | |
| WO | 8903038 | | 4/1989 | |
| WO | WO 89/03038 | * | 4/1989 | .......... G01N/33/48 |

OTHER PUBLICATIONS

Zhang et al."Use of microwaves in Immunoenzyme techniques." Clinical Chemistry, vol. 39, No. 9, 1993, p. 2021.*

Patent Abstracts of Japan Publication No. 08082627 dated Mar. 26, 1996.

Budde, U., et al. "Drastische Verkurzung von Inkubationszeiten . . . Mikrowellengeraten" Infusionsther Transfusionsmed, vol. 22, Supp. 1, p. 92–94, (1995) English Abstract.

Zhang, L., et al. "Use of Microwaves in Immunoenzyme Techniques" Clinical Chemistry, vol. 39, No. 9, p. 2021, (1993).

Marani, E. "Microwave Applications in Neuromorphology and Neurochemistry: Safety Precautions and Techniques" A Companion to Methods in Enzymology, vol. 15, p. 87–99, (1998).

Van Dorp, R., et al. "ELISA Incubation Times can be Reduced by 2.45–GHz Microwaves" J. Clin.Lab.Immunol., vol. 34, p. 87–96, (1991).

Van Dorp, R., et al. "A Rapid ELISA for Measurement of Anti–Glomerular Basement Membrane Antibodies using Microwaves" J.Clin.Lab.Immunol., vol. 40, p. 135–147, (1993).

* cited by examiner

Primary Examiner—Christopher L. Chin
Assistant Examiner—Lisa V. Cook
(74) Attorney, Agent, or Firm—Ladas & Parry

(57) ABSTRACT

This invention relates to a rapid and efficient method for carrying out enzyme-linked immunosorbent assay for detection of minute quantities of biomolecules such as antigen, antibody etc. This invention particularly relates to microwave mediated immobilization of antigen or antibody on to the activated surface followed by performing subsequent steps of ELISA by controlled microwave irradiation. The invented procedure has dramatically reduced the total time required for ELISA to less than 10 minutes from hours to days. The invented ELISA procedure is rapid, economical, reproducible and simple and can be automated. The invented procedure is useful for carrying out ELISA in clinical diagnostics, molecular biology, agriculture, sericulture, food technology, environmental science, biomedical research and other related fields.

14 Claims, No Drawings

RAPID METHOD FOR ENZYME-LINKED IMMUNOSORBENT ASSAY

CROSS REFERENCE TO RELATED APPLICATIONS

The present application claims priority under 35 U.S.C. §119 from PCT/IN 00/00075 filed on Aug. 16, 2000.

FIELD OF THE INVENTION

The invention relates to a rapid method for carrying out microwave mediated ELISA (MELISA). More particularly, this invention relates to a rapid and efficient method for microwave mediated ELISA (MELISA) wherein all the major steps of ELISA can be performed under microwave irradiation in short time. This method is useful in clinical diagnostics, molecular biology, agriculture, food technology, environmental science etc.

The invented ELISA method is simple, time saving and obviates the time consuming cumbersome procedure. This method has the potential for automation.

This method has the advantage over the existing methods for ELISA which take long time usually ranging from several hours to 2 days whereas the invented method takes less than 10 minutes. It is particularly useful for disease diagnosis where quick results are required.

BACKGROUND OF THE INVENTION

Enzyme linked immunosorbent assay (ELISA) is a very sensitive technique used for semiquantitative or quantitative determination of the concentration of certain antigens and antibodies. ELISA has become a useful tool in disease diagnosis in both animals and plants. Apart from this, its other applications include screening of monoclonal antibodies during the course of their production (Douillard, J. Y. and Hoffman, T., 1983), pesticide residue detection in crop produce (Van Emon, J. M. and Lopez-Avila, V., 1992) and environmental samples like soil and water (Linde, D. G. and Goh, K. S., 1995), detection of apoptosis in tissue culture etc. (Salgame, P. et al, 1996). Polystyrene microtitre plate is used universally for carrying out ELISA, as it is transparent, cheap, easily available, can be moulded to any desired shape and has a property of binding proteins through adsorption. Conventional methods of ELISA are based on the immobilization of antigen or antibody onto the surface of the wells of a polystyrene microtitre plate through adsorption. This is attributed to the non-covalent interaction between the biomolecule and the polystyrene surface.

However, adsorption is usually too inefficient a process to give good yields and doesn't always proceed in a dose dependent manner. To overcome the inefficiency of conventional methods covalent immobilization of biomolecules onto the microtitre plate has been carried out by many (Satoh, A. et al, 1999). Covalent binding of immunogens to grafted plastic surfaces has also been reported (Larsson, P. H. et al, 1987). Despite this, the conventional ELISA method requires very long time varying from several hours to 2 days for completion. This is the main drawback of different ELISA methods, either based on adsorption or covalent binding. In case of medical urgency precious time is lost in diagnosis before the patient could be given medication. In agriculture, ELISA is usefull for detecting pesticide residues in crop produce and environmental samples. Export and marketing of crop produce can be delayed as a consequence of this handicap in the ELISA method, which contributes to loss of valuable foreign exchange.

The applicants have developed a novel and unique method whereby ELISA can be carried out rapidly by the use of microwaves. Microwaves are known for accelerating immunohistochemistry for about a decade (Boon, M. E. and Kok, L. P., 1992; Boon, M. E. et al, 1989; Boon, M. E. et al, PCT patent application WO 89/ 03038; Chiu, K. Y. and Chan, K. W., 1987; Hjerpe, A. et al, 1988).

Covalent immobilization of antigen or antibody on to a polystyrene surface by microwave irradiation has not been reported so far. In fact, all the major steps of ELISA by microwave irradiation in such a short time to detect minute quantities of antigen or antibody by measuring optical density was not known in the prior art.

However, there are attempts for doing one of the steps of ELISA by microwave irradiation (Hierpe, A. et al, 1988) where polystyrene ELISA plates were coated first with rabbit anti-carcinoembryonic antigen by incubating over night at 4° C., followed by incubation of the antigen (CEA). In the subsequent step i.e. after the addition of enzyme-linked antibodies the authors studied the effect of microwave irradiation on antigen-antibody reactions.

In another experiment by the same authors, ELISA plates were first coated with normal mouse serum by incubating over night at 4° C., followed by overnight incubation with non-labeled rabbit anti-mouse Ig. In the subsequent step they added mouse PAP (peroxidase-antiperoxidase) complexes and determined the effect of microwave irradiation on the reactivity constants of reactions of this last step.

In third experiment Hjerpe et.al first coated the plates with non-specific mouse serum followed by incubation with biotinylated horse-anti-mouse IgG. The plates were then used to study the effect of microwaves upon the subsequent binding of biotin-avidin complexes.

The reaction yields in all the above experiments were smaller in samples subjected to microwave irradiation as compared to those processed without microwave stimulation. The experiments showed that the microwaves caused a major loss of reactivity and the total yields were approximately 10% to 15% compared to conventional one that was carried out outside the microwave oven. According to authors, the diminished value in the microwave technique may be due to too high temperatures in the wells, despite the fact that a water load (a beaker of water to absorb excess microwave energy) and chilled bottom plate were taken as a precautionary measure.

In further ELISA experiment authors (Koh and Boon, 1992) used a fiberoptic thermometer to restrict the temperature below 40° C. Here also a water load of 200 ml tap water was taken. Besides, the fluid in the wells was stirred by slowly blowing air through the solution via thin plastic tips, which were inserted into the wells. In an experiment the authors carried out only two steps namely, antibody and conjugate binding steps by microwave irradiation for 6 minutes at 150 watts each.

In another experiment, antibody, antigen and conjugate binding steps were carried out in 15, 30 and 30 minutes respectively using 45–50% microwave power in each step.

Remaining steps in both the experiments were carried out by conventional procedure. But the ELISA values were found to be much less in the above experiments than the conventional method.

According to authors, the longer exposure time gave higher extinction value (ELISA value) but the time gain was not attractive. In fact there was no benefit when exposure time of 30 minutes or more were used. Too short exposure times led to extinction values which, were rather low and could not be used.

The reported methods of ELISA by microwave exposure has several drawbacks such as (1) the results (ELISA value) were much less than the conventional procedure, (2) the time gain was not attractive. It may be possible to get comparable results (ELISA value) by doing the ELISA out side microwave oven in the same time, (3) procedure required water load, (4) it required cooling system or chilled bottom plate, (5) it needed a stirring system in the well of the microtitre plate, (6) not all the steps were carried out by microwave energy and the reported ELISA procedure has little or no potential for automation.

The applicants in the present invention have overcome all the above drawbacks. In fact, like thermal energy microwave can also activate or inactivate a biomolecule. Without proper conditions the microwave may cause partial or total destruction of the biomolecule leading to low or undesirable ELISA value. In the invented procedure proper conditions were found, most of, which are contrary to the reported method, or not known in the prior art. In the invented method all the steps except color development are carried out by microwave stimulation. Blocking step was not carried out by microwave irradiation in the published procedure as it gave nonspecific binding, whereas the applicants have invented a method where blocking step is carried out in short time by microwave irradiation. Longer microwave exposure time gave higher ELISA value in the reported method whereas in the invented procedure, it leads to destruction of material or nonspecific binding. This may be because water load or the cooling system used in the reported method absorbed most of the microwave energy giving minimum microwave effect and a significant effect of time as in the conventional method. In contrast, the invented method does not require any water load, cooling system or stirring system. Moreover, in the invented method about 200 times less (excluding color development step) time requires for ELISA than the conventional one (which takes around 18 hours) with comparable or even better ELISA value. Hence, it also has a great potential for automation.

The reported ELISA was carried out on a microtitre plate that did not bind the biomolecule through covalent linkage. In fact, it is known that the microwaves may readily effect the integrity of the noncovalent secondary bonding, such as hydrogen bonds, hydrophobic interactions and Van der Waal's interaction.

OBJECTS OF THE INVENTION

The main object of the present invention is to provide a rapid and efficient method for enzyme linked immunosorbent assay to detect minute quantities of antigen or antibody spectrophotometrically for rapid diagnosis of diseases.

Another object of the present invention is to provide a technique, which is simple, reproducible and does not require additional expertise or costly equipment.

Another object of the present invention is to provide a rapid technique, which has the potential for automation and which can minimize human error that usually varies from person to person.

SUMMARY OF THE INVENTION

With a view to achieve the objects and overcoming the disadvantage of known ELISA method, a rapid and efficient method is provided for microwave mediated ELISA (MELISA) which comprises the steps of (i) covalent immobilization of the antigen or antibody on to the activated solid surface by microwave irradiation, (ii) blocking the free surface with blocking agent by brief microwave irradiation, (iii) binding of antibody or antigen by controlled microwave irradiation (iv) binding of conjugate by controlled microwave irradiation, (v) adding dye-substrate to the wells and (vi) recording the absorbance value.

Microwave mediated ELISA (MELISA) procedure is carried out on an activated surface in a very short time (around 10 minutes) and with the same efficacy as in the conventional ELISA carried out at 37° C., in 16–18 hours.

This invention has the potential of automation or semi automation of the ELISA procedure.

Microwaves are known to effect the integrity of the noncovalent secondary bonding, such as hydrogen bonds, hydrophobic interactions and Van der Waal's interaction.

To overcome this problem the applicants activates the surface of the microtitre wells prior to use. The activated surface immobilizes the antigen through a covalent bond by a brief microwave exposure. This covalently immobilized antigen is stable enough to withstand repeated but brief microwave exposure, which were needed for performing the subsequent steps of ELISA. Subsequent steps of biomolecule binding in the ELISA procedure are through non covalent binding which are susceptible to microwave energy. These problems are overcome by controlling the time and energy of the microwave irradiation in each step.

Novelty of the present invention is that the ELISA is carried out on to an activated surface capable of forming covalent linkage with the proteinaceous ligand.

Microwave mediated covalent immobilization of biomolecule, more preferably antigen or antibody on to the activated surface is another novelty of this invention.

Controlled microwave irradiation in each step of ELISA procedure is another new approach.

In the invented procedure, all the steps of ELISA such as antigen binding, blocking, antibody and conjugate binding are carried out by microwave irradiation and only enzyme-substrate reaction is performed out side microwave oven at room temperature. The invented procedure of ELISA is very fast with comparable or even better ELISA value than the conventional method.

Another novelty of the present invention is that the invented ELISA procedure does not require any water load or stirring system.

Another novelty of the present invention is that the invented ELISA procedure can be fully or partially automated with the use of a specially designed device.

Another novelty of the present invention is that the invented procedure can be used for other immunoassays like radio immunoassay, radio-immunosorbent test, radio allergosorbent test, biotin- avidin /streptavidin immunoassay, immnunoblotting, immunostaining etc. apart from different types of ELISA such as direct ELISA, indirect ELISA, sandwich ELISA and alike.

DETAILED DESCRIPTION OF THE INVENTION

The present invention provides a new approach for enzyme linked immunosorbent assay technique on an activated microtitre plate, module or well by microwave exposure. Activated surface immobilizes the antigen through covalent bonding by microwave irradiation. This covalently immobilized antigen is stable enough to withstand repeated but brief microwave exposure, which are needed for performing the subsequent steps of ELISA. ELISA is a multistep and delicate process where improper condition in any step may hamper the whole results.

In the invented procedure inert solid surface such as polystyrene is activated by photochemical reaction in dry condition using a photoactivable compound. Activation of the solid support is made by exposing the support coated with the photoactivable compound to UV radiation or bright sunlight. This activated support is used for microwave mediated ELISA (MELISA) and for control ELISA to detect antibodies, to example E.histolytica and Aspergillus fumigatus. When untreated support is used it failed to bind the biomolecule in such a short time by microwave irradiation.

Microwave irradiation is performed inside a domestic microwave oven (BPL-Sanyo, India), operating at a frequency of around 2450 MHz.

The amoebic antigen is obtained from the culture of E.histolytica as per published procedure (Sawhney, S., et al, 1980; Sharma, G. L, et al, 1984). The protein concentration of the antigens was 1.54 mg per ml as determined by the method of Lowry etal. (Lowry, O. H., et al, 1951). The antigen was diluted before performing ELISA and a concentration of 1.0 μg per well was used for coating the wells.

Phosphate buffer saline (PBS), pH 7.2, 0.01 M is used as coating buffer.

Phosphate buffer saline (PBS), pH 7.2, 0.01 M together with 0.1% tween 20 (polyoxyethylene 20 sorbiton monolaurale is used as washing buffer.

Blocking solution is made by dissolving 2% BSA in 0.01 M PBS, pH 7.2.

Substrate solution is prepared by adding 0.067% of o-phenylenediamine and 0.043% of $H_2O_2$ in 0.1 M phosphate citrate buffer, pH 4.5).

Hyperimmune sera to E.histolytica is raised in Newzealand White rabbits as per the methods of Sawhney et al (Sawhney et. al, 1980). The antibody titres in the sera are checked by gel-diffusion test.

The antibody (+ve sera) is diluted before performing ELISA and 1:300 dilution in PBS is used for the experiments.

Rabbit is bled through the ear vein before giving the immunization dose of E.histolytica antigen to obtain negative control sera (–ve sera). 100 μl of diluted (1:300) –ve sera is used for each well.

Horse radish peroxidase conjugated anti-rabbit IgG is purchased from Sigma as lyophilized powder.

After reconstitution, the optimum dilution is found to be 1:4000 as determined by checkerboard titration, which is used in the experiments.

ELISA is a 5-step procedure, namely antigen binding, blocking, antibody binding, conjugate binding and color development. Each step of MELISA is optimized by carrying out the subsequent steps by conventional ELISA procedure. Conventional ELISA is carried out by overnight coating the activated wells with antigen at 4° C., blocking the wells in 2 hours at 37° C. followed by antibody and conjugate binding at 37° C. for 2 h each and color development that is enzyme-substrate reaction at room temperature for 5 minutes followed by reading absorbance.

In the invented procedure, the first step of ELISA is performed by covalent immobilization of the amoebic antigen onto the activated polystyrene microwell plate by microwave irradiation at 700 watts in different duration of time. Binding, is detectable even in 10 seconds which increases with the increase in time of irradiation (Table 1). At 90 seconds the antigen binding becomes more or less same as 70 seconds of microwave irradiation. Hence, optimum time for antigen immobilization is taken as 70 seconds. In control experiments carried out for the same duration that is 70 seconds at 37° C., no binding of antigen to the activated polystyrene surface is observed.

In the second step of MELISA, blocking is carried out with 2% BSA in 10 seconds in the microwave oven at a power out put of 700 watts to block the free surface of the activated surface. Further increase in irradiation time showed non-specific binding (Table 2.)

In the third step of MELISA, antibody binding to the immobilized antigen is carried out at 155 watts for 100 seconds. This is a crucial step where harsh conditions such as excess time or higher power output leads to nonspecific binding as shown in Table-3. At 155 watts in 50 seconds and 100 seconds, no nonspecific binding is observed. Although the observed OD is very low in 50 seconds, 100 seconds is found to be excellent, giving high ratio of –ve to +ve sera. Increase in time to 150 seconds increases the nonspecific binding (table 4).

In the fourth step of MELISA, conjugate binding is carried out by microwave irradiation at 155 watts for different duration of time. Excellent result is obtained in 100 seconds (Table 6). Harsh condition such as excess time or higher energy such as 700 watts leads to nonspecific binding (Table 5).

In each step control experiment is carried out by doing the same experiment outside microwave oven for the same duration of time. In all this experiments negligible or undesirable ELISA value (nonspecific binding) is obtained.

After optimizing each step of MELISA, the applicants carried out all the steps with optimized conditions of microwave irradiation without damaging the biomolecules. To achieve it the applicants have immobilized antigen on to the activated well in 70 seconds, blocking in 10 seconds, antibody binding in 100 seconds and conjugate binding at 100 seconds of irradiation. The total time required for all these steps are 280 seconds only by the invented procedure whereas conventional ELISA is done in about 18 hours.

MELISA and ELISA to detect E.histolytica antibodies are repeated several times under similar experimental conditions and the results are found to be highly reproducible as shown in Table- 7.

MELISA procedure is further verified by detecting Aspergillus fumigatus antibody from patients sera. A. fumigatus antigen is obtained from static culture as per published procedure (Banerjee, B., et al, 1990).

The protein concentration of the antigens is found to be 12.5 mg per ml as determined by the method of Lowry et.al. (Lowry et.al., 1951). Immunoreactivity of the antigen is checked by using hyperimmune serum raised in Newzealand White rabbits.

Sera samples are obtained from 10 patients of allergic bronchopulmonary aspergillosis (ABPA). All these patients fulfill the clinical criteria of ABPA as described earlier (Rosenberg, M., et al, 1997).

Negative control sera samples are taken from 10 volunteers who are apparently healthy and do not have any respiratory or other disease.

Pooled positive and negative sera are taken as the controls for ELISA, which are found to be comparable in both MELISA and conventional ELISA.

Horse radish peroxidase conjugated with anti-human IgG is purchased from Sigma as lyophilized powder. After reconstitution, the optimum dilution of the conjugate is found to be 1:4000 as determined by checkerboard titration.

A.fumigatus antibody (present in patient sera) detected by the invented method is in agreement with the conventional ELISA procedure (Table. 8)

The results obtained in different experiments are given comparative grades as below:

Excellent=++++
Very good=+++
Good=++
Poor=+
Undesirable or no results=−

The total time required for MELISA is less than 10 minutes. However, time required in each step may vary depending on the biomolecules where excellent results can be obtained by minor modification of reaction conditions that is minor alternation in duration and energy of irradiation.

Accordingly the present invention provides a rapid method for microwave mediated enzyme-linked immunosorbent assay characterized in using an activated solid support wherein the said method comprises:

(a) providing an activated solid support, (b) loading a biomolecule selected from an antigen or antibody by dissolving the said biomolecule in a coating buffer into the activated well of the said solid support and placing the said well inside a microwave oven followed by irradiating the said well with microwaves at a frequency ranging between 2300–2500 MHz with the power output ranging between 600–900 watts for a period ranging from 50–100 seconds followed by washing the well thoroughly with an appropriate washing buffer, (c) blocking the free sites of the well with an immobilized biomolecule as obtained from step (b) as above by loading blocking solution into the said well and irradiating it inside the microwave oven at a frequency of from 2300–2500 MHz with a power out put ranging between 600–800 watts for a period ranging from 5–20 seconds and washing the said well with an appropriate washing buffer, (d) loading the corresponding antibody or antigen dissolved in a buffer into the well immobilized with antigen or antibody as obtained from step (c) above followed by irradiation of said well inside the microwave oven at a frequency of from 2300–2500 MHz with a power output ranging from 50–200 watts for a period ranging from 90–200 seconds followed by washing with washing buffer, (e) loading an appropriate enzyme- conjugate dissolved in a suitable buffer into the above said well obtained from step (d) and irradiating the said well inside a microwave oven at a frequency of from 2300–2500 MHz with a power output ranging from 100–300 watts for a period ranging from 50–150 seconds followed by washing with a washing buffer, (f) adding a substrate-dye-buffer to the above well as obtained from step (e) as above and keeping it for a period ranging from 4 to 10 minutes in dark followed by addition of stop solution and measuring optical density of the solution by spectrophotometer at a suitable wavelength.

In an embodiment of the present invention the solid support used is selected from the group consisting of materials such as polystyrene, polypropylene, polyethylene, glass, cellulose, nitrocellulose, silicagel, polyvinyl chloride, polyaniline and alike.

In an embodiment of the present invention the preferred solid support used is polystyrene.

In yet another embodiment the solid support is selected from any shape, form and size such as sheets, plates, test particles such as beads and microspheres, test tubes, test sticks, test strips, well, ELISA plate, microwell plate or module.

In an embodiment of the present invention the solid support used for immobilizing biomolecules is selected from any support having at least one active functional group capable of binding ligand molecules by covalent means.

In yet another embodiment of the present invention the functional group is selected from halide, aldehyde, acetyl, epoxide, succinamide, isothiocyanate, acylazide and alike.

In yet another embodiment of the present invention the functional group may be present in the support itself or can be introduced by conventional chemical or photochemical or other methods known to prior art.

In yet another embodiment of the present invention the functional group is introduced on to the solid support by photochemical reaction in dry condition using a photoactivable compound which is selected from 4-fluoro-3-nitroazidobenzene, N-hydroxysulfo-succinimidyl 4-azidobenzoate, N-hydroxysulfo-succinimidyl 4-azidosalicyclic acid and alike.

In yet another embodiment of the present invention polystyrene surface is activated by coating with 1-flouro-2-nitro-azidobenzene and exposing the coated support in dry condition to UV radiation at 365 nm.

In yet another embodiment of the present invention the light source for photochemical reaction is selected from UV lamp, laser beam, bright sunlight or alike.

In yet another embodiment of the present invention time for photoreaction for activation of solid support is selected form 10 seconds to 10 hours.

In yet another embodiment microwave irradiation is performed in a microwave apparatus selected from domestic microwave oven, specially designed microwave oven or any apparatus or chamber in which microwave is generated and alike.

In yet another preferred embodiment of the invention, the first step of ELISA, is carried out by covalent binding of antigen or antibody onto the activated plate by microwave irradiation at a frequency of from 2300–2500 MHz with the power output ranging between 600–900 watts for a short period ranging from 50–100 seconds.

In yet another preferred embodiment of the invention the second step of ELISA, that is the blocking step is carried out by microwave irradiation at a microwave frequency of from 2300–2500 MHz with a power out put ranging between 600–800 watts for a short period ranging from 5–20.

In yet another preferred embodiment of the invention the third step of ELISA, that is corresponding antibody or antigen binding is carried out by microwave irradiation at the microwave frequency of from 2300 to 2500 MHz with power output of from 50 to 200 watts in a period ranging from 90 to 200 seconds.

In yet another preferred embodiment of the invention the fourth step of ELISA, that is enzyme-conjugate binding is carried out by microwave irradiation at the microwave frequency of from 2300 to 2500 MHz with power output of from 100 to 300 watts in a period ranging from 50 to 150 seconds.

In yet another preferred embodiment of the invention the total time for antigen binding, blocking, antibody binding and conjugate binding is ranging from 195 to 470 seconds wherein the total time for conventional method usually is ranging from 10 hours to 24 hours.

In another embodiment to the present invention, the antigen can be dissolved in a coating buffer of suitable composition having a pH, in the range of from 6.5 to 11 with molarity ranging from 0.005 M to 0.1 M compatible with the antigen such as carbonate buffer, phosphate buffer and alike.

In yet another preferred embodiment of the invention, washing buffer used is a mixture of phosphate buffer having a pH, in the range of from 6.5 to 11, with molarity ranging from 0.005 M to 0.1 M and tween 20 in the range between 0.05% to 3%.

In yet another preferred embodiment of the invention, blocking reagent is selected from bovine serum albumin, skimmed milk powder, gelatin and alike.

In another embodiment to the present invention biomolecule is selected from antigen or antibody. Antigen may be any, biomolecule, microorganism, substance etc. that elicits or has the potential to elicit an immune response.

In yet another preferred embodiment of this invention, antibody is selected from any biomolecule, which is produced by the host in response to inoculation with the specific antigen and has capabilities of binding to the antigen in a specific manner.

In yet another preferred embodiment of this invention, conjugate is a specific biomolecule having antibody or antigen conjugated with an enzyme selected from peroxidase or alkaline phosphatase.

In yet another preferred embodiment of this invention, enzyme may be replaced by a label selected from chromophore, fluorophore and alike which facilitates its assay.

In yet another preferred embodiment of this invention, the invented procedure can be used for other immunoassays like radio immunoassay, radio-immunosorbent test, radio allergosorbent test, biotin- avidin/streptavidin immunoassay, immnunoblotting, immunostaining etc. apart from different types of ELISA such as direct ELISA, indirect ELISA, sandwich ELISA and alike.

The invention further provides an apparatus for microwave mediated enzyme linked immunosorbent assay (MELISA) comprising (a) a loading chamber, for loading the samples or reagents from a specified bottle from a fine tube by a suitable pump onto the activated polystyrene plate/module automatically; (b) a reaction chamber consisting of magnetron, exhaust fan etc. for carrying out all the steps such as binding of the antigen, blocking, antibody binding and antibody enzyme conjugate binding by microwave irradiation and enzyme substrate reaction without microwave stimulation at ambient temperature in a pre-programmed time; (c) a washing cum drying chamber for washing and drying the said ELISA plate or module automatically by a pre-programmed command after each step of the MELISA procedure; (d) a detection chamber for calorimetric detection with the help of the spectrophotometer; (e) a moving platform is used for carrying the Elisa plate/modules from one chamber to another chamber (f) a microprocessor based computing means for controlling MELISA method through suitable hardware and software.

This invention is further explained with the help of the following examples and should not be construed to limit the scope of the invention.

EXAMPLE 1

Activation of Solid Support

Wells of a module (12 well polystyrene module, Dynatech, USA) are loaded with 1.82 mg 1-flouro-2-nitro-azidobenzene (FNAB), dissolved in 100 µl of methanol per well and dried properly in the dark. FNAB coated wells are then irradiated for 10 min. by UV light at 365 nm in a UV Stratalinker 2400 (Stratagene®, USA) or kept under bright sunlight for 1 h. The wells are then washed several times with methanol to remove the unbound linker and dried at room temperature. These activated wells of the module are used for immobilization of antigens or antibodies in the invented procedure.

EXAMPLE 2

Immobilization of Entamoeba histolyica Antigen by Microwave Irradiation.

E. histolytica antigen (1 µg) diluted in 100 µl PBS is loaded into an activated well of a module and subjected to microwave irradiation for 10 seconds inside a domestic microwave oven (BPL-Sanyo, India), operating at a frequency of around 2450 MHz with a maximum power output of around 700 watts. Irradiation is conducted in the microwave oven with the highest power setting of 10, that is the magnetron duty cycle of 100% of an output power of 700 watts.

The well is thoroughly washed with washing buffer so as to remove the unbound antigen. Subsequent steps are carried out by conventional procedure. Thus, blocking with blocking solution (200 µl ), antibody (100 µl ) binding and anti rabbit IgG-horse radish peroxidase conjugate (100 µl) binding are carried out by incubation at 37° C. for 2 hours each. The well is washed thoroughly after each step by washing buffer. Color development is done using 100 µl of substrate solution. The well is read at 490 nm in an ELISA Reader (Spectramax 190 microplate spectrophotometer, Molecular Devices Corporation, California 94089) and absorbance values are recorded. All the experiments are performed in triplicate wells. Similar experiments are conducted with –ve sera.

A control experiment using microwaves is carried out in a similar manner using untreated wells. Another control experiment is performed using the activated wells by incubating the antigen at 37° C. for the same duration as is done under microwaves. There is no immobilization of antigen in both the control reactions. The whole experiment is separately repeated by varying the time for antigen binding viz. 30, 50, 70, and 90 seconds each. The results for optimization of antigen binding time for microwave irradiation are given in Table-1

EXAMPLE 3

Blocking of Free Surface with Blocking Agent by Microwave Irradiation.

E. histolytica antigen is immobilized by microwaves in an activated well of a module in 70 seconds as above. After thorough washing with washing buffer 200 µl of blocking solution is added to the well and irradiated with microwaves at 700 watts for 10 seconds. Subsequent steps of antibody and conjugate binding are done outside microwave oven as described in example 2. Color development and absorbance reading are also done as in example 2.

Similar experiments are conducted with –ve sera. To check the optimum time for blocking, two different experiments are carried out in a similar manner except the microwave exposure time is increased to 40 and 60 seconds. All the experiments are performed in triplicate wells. The results for optimization of blocking time under microwave irradiation are given in Table-2.

EXAMPLE 4

Antibody Binding by Microwave Irradiation at High Energy Level.

E. histolytica antigen is immobilized onto the activated well of a module by microwaves at 700 watts in 70 seconds followed by blocking of free surface with blocking agent by microwave irradiation at 700 watts for 10 seconds as in example 3. Antiamoebic antibody (100 μl) is loaded into the well. The well is then exposed to microwaves for 10 seconds at 700 watt. After washing the wells properly with washing buffer, binding of conjugate and subsequent color development are carried out as in example 3. Similar experiments are conducted with –ve sera. The experiment is repeated varying the time of microwave exposure at 30, 50, 70 and 90 seconds for binding antibodies, keeping all other conditions similar. All the experiments are performed in triplicate wells. The results for antibody binding by microwave irradiation at high energy level are shown in Table-3.

EXAMPLE 5

Antibody Binding by Microwave Irradiation at Low Energy Level.

The experiments are performed here for antibody binding in the similar conditions as described in example 4, except that the antibody binding step is performed at a low energy level that is at 155 watts. Time of microwave exposure is 10, 50, 100 and 150 seconds respectively for four different sets of experiments. The results for antibody binding by microwave irradiation at low energy level are shown in Table-4.

EXAMPLE 6

Conjugate Binding by Microwave Irradiation at High Energy Level.

E. histolytica antigen is immobilized onto an activated well by microwaves at 700 watts in 70 seconds followed by blocking by microwaves at 700 watts for 10 seconds and antibody binding at 155 watts in 100 seconds as in example 5.

100 μl of anti rabbit IgG-horse radish peroxidase conjugate is loaded into the well and is subjected to microwave irradiation at 700 watts. Time of microwave exposure is 5, 10, 15 and 20 seconds respectively for four different sets of experiments keeping all other conditions similar as in example 5. All the experiments are performed in triplicate wells. The results for conjugate binding by microwave irradiation at high energy level are shown in Table-5.

EXAMPLE 7

Conjugate Binding by Microwave Irradiation at Low Energy Level

The experiments are performed here for second antibody-conjugate binding in the similar conditions as described in example 6, except that the second antibody-conjugate binding step is performed at a low energy level that is at 155 watts. Time of microwave exposure is kept at 50, 100 and 120 seconds respectively for four different sets of experiments. The results for conjugate binding by microwave irradiation at low energy level are shown in Table-6.

EXAMPLE 8

Detection of E. histolytica Antibodies by Microwave Mediated Enzyme-Linked Immunosorbent Assay (MELISA) and Enzyme-Linked Immunosorbent Assay (ELISA)

E. histolytica antigen is immobilized onto the activated well by microwaves at 700 watts in 70 seconds, blocked with blocking solution by microwaves at 700 watts for 10 seconds, antibody binding at 155 watts in 100 seconds followed by antibody-conjugate binding at 155 watts in 100 seconds as described in above examples. Similar experiments are conducted with –ve sera. All the experiments are performed in duplicate wells and repeated for 5 times. After each step thorough washing are done by washing buffer.

Conventional ELISA is performed with same reagents, substrate and buffer except that all the steps are carried out without microwave stimulation. Thus, ELISA is carried out by coating the activated wells with antigen overnight at 4° C., followed by blocking, antibody and conjugate binding at 37° C. for 2 h each. Color development is same for the invented and the conventional procedure. The results for the detection of E. histolytic antibodies by Microwave mediated Enzyme-Linked Immunosorbent Assay (MELISA) and Enzyme-Linked Immunosorbent Assay (ELISA) are presented in the Table-7

EXAMPLE 9

Detection of A. fumigatus Antibodies by Microwave mediated Enzyme-Linked Immunsorbent Assay (MELISA) and Enzyme-Linked Immunosorbent Assay (ELISA)

Detection of A. fumigatus antibodies in patients sera is carried out by Microwave mediated Enzyme-Linked Immunosorbent Assay (MELISA) and Enzyme-Linked Immunosorbent Assay (ELISA) method in a similar conditions as described in example 8, except that the antigen is A. fumigatus, antibody is from 10 different patients sera, control sera having no specific antibody is from healthy volunteers and the conjugate is anti human IgG-peroxidase. All the experiments are performed in duplicate wells. The results for the detection of A. fumigatus antibodies by Microwave mediated Enzyme-Linked Immunosorvent Assay (MELISA) and Enzyme-Linked Immunosorbent Assay (ELISA) are presented in the Table-8

TABLE 1

Detection of E. histolytica antibodies by carrying out first step by MELISA and remaining steps by ELISA procedure.
MELISA: Step-1. Immobilization of antigen by microwave irradiation at 700 watts onto the activated wells in different times as in the table, control: 37° C., 70 seconds
ELISA: (Step - 2 to 5) Conventional procedure

| Time (in sec) | + ve sera | | | – ve sera | | | Remarks |
|---|---|---|---|---|---|---|---|
| 10 | 0.188 | 0.196 | 0.191 | 0.002 | 0.004 | 0.003 | + + |
| 30 | 0.208 | 0.193 | 0.198 | 0.005 | 0.001 | 0.002 | + + |
| 50 | 0.226 | 0.211 | 0.214 | 0.006 | 0.002 | 0.004 | + + + |
| 70 | 0.363 | 0.355 | 0.358 | 0.005 | 0.001 | 0.003 | + + + + |
| 90 | 0.370 | 0.360 | 0.367 | 0.0O1 | 0.003 | 0.004 | + + + + |
| Control | 0.003 | 000O1 | 0.004 | 0.006 | 0.004 | 0.002 | |

TABLE 2

Detection of E. histolytica antibodies by carrying out first two steps by MELISA and remaining steps by ELISA procedure.
MELISA: Step-1. Ag binding- 70 seconds, 700 watts. Step-2. Blocking- variable time as in the table, 700 watts.
ELISA: (Step - 3 to 5) Conventional procedure.

| Time (in sec) | + ve sera | | | – ve sera | | | Remarks |
|---|---|---|---|---|---|---|---|
| 10 | 0.270 | 0.288 | 0.273 | 0.006 | 0.005 | 0.008 | + + + |
| 40 | 0.352 | 0.377 | 0.367 | 0.098 | 0.092 | 0.094 | + + |
| 60 | 0.293 | 0.290 | 0.287 | 0.283 | 0.270 | 0.276 | – |

TABLE 3

Detection of E. hislolytica antibodies by carrying out first three steps by MELISA and remaining steps by ELISA procedure. MELISA: Step-1. Ag binding- 70 seconds, 700 watts. Step-2. Blocking- 10 seconds, 700 watts. Step-3. Antibody binding-variable time as in the table, 700 watts. ELISA; (Step - 4 & 5) Conventional procedure.

| Time (in sec) | + ve sera | | | − ve sera | | | Remarks |
|---|---|---|---|---|---|---|---|
| 10 | 0.216 | 0.203 | 0.211 | 0.087 | 0.123 | 0.098 | + |
| 30 | 0.392 | 0.353 | 0.388 | 0.100 | 0.137 | 0.114 | − |
| 50 | 1.413 | 1.177 | 1.213 | 0.194 | 0.180 | 0.194 | + + |
| 70 | 1.313 | 1.253 | 1.276 | 1.263 | 1.279 | 1.275 | − |
| 90 | 1.287 | 1.239 | 1.238 | 1.288 | 1.248 | 1.234 | − |

TABLE 4

Detection of E. histolytica antibodies by carrying out first three steps by MELISA and remaining steps by ELISA procedure. MELISA: Step-1. Ag binding- 70 seconds, 700 watts. Step-2. Blocking- 10 seconds, 700 watts. Step-3. Antibody binding-variable time as in the table, 155 watts. ELISA (Step - 4 to 5): Conventional procedure.

| Time (in sec) | + ve sera | | | − ve sera | | | Remarks |
|---|---|---|---|---|---|---|---|
| 10 | 0.010 | 0.014 | 0.016 | 0.004 | 0.005 | 0.007 | − |
| 50 | 0.079 | 0.087 | 0.82 | 0.003 | 0.006 | 0.005 | + |
| 100 | 0.511 | 0.524 | 0.530 | 0.014 | 0.027 | 0.020 | + + + + |
| 150 | 0.256 | 0.276 | 0.289 | 0.218 | 0.221 | 0.223 | − |

TABLE 5

Detection of E. histolytica antibodies by carrying out first four steps by MELISA and last step by conventional procedure. MELISA Step-1. Ag binding- 70 seconds, 700 watts. Step-2. Blocking- 10 seconds, 700 watts. Step-3. Antibody binding- 100 seconds, 155 watts. Step-4. Conjugate binding- variable time as in the table, 700 watts. Step - 5. Color development- 5 minutes at room temperature.

| Time (in sec) | + ve sera | | | − ve sera | | | Remarks |
|---|---|---|---|---|---|---|---|
| 5 | 0.147 | 0.136 | 0.138 | 0.032 | 0.020 | 0.23 | + + |
| 10 | 0.166 | 0.166 | 0.168 | 0.087 | 0.093 | 0.85 | + |
| 15 | 0.192 | 0.171 | 0.183 | 0.110 | 0.119 | 0.116 | − |
| 20 | 0.388 | 0.503 | 0.446 | 0.312 | 0.288 | 0.293 | − |

TABLE 6

Detection of E. histolytica antibodies by carrying out first four steps by MELISA and last step by conventional procedure. MELISA: Step-1. Ag binding- 70 seconds, 700 watts. Step-2. Blocking- 10 seconds, 700 watts. Step-3. Antibody binding- 100 seconds, 155 watts. Step-4. Conjugate binding- variable time as in the table, 155 watts. Step - 5. Color development- 5 minutes at room temperature.

| Time (in sec) | + ve sera | | | − ve sera | | | Remarks |
|---|---|---|---|---|---|---|---|
| 50 | 0.205 | 0.189 | 0.192 | 0.021 | 0.018 | 0.022 | + + |
| 100 | 0.558 | 0.532 | 0.543 | 0.036 | 0.031 | 0.032 | + + + + |
| 120 | 0.145 | 0.193 | 0.157 | 0.023 | 0.014 | 0.023 | + |

TABLE 7

Detection of E. histolytica antibodies: Comparison of MELISA and ELISA procedures.
MELISA: Step-1. Ag binding- 70 seconds, 700 watts. Step-2. Blocking- 10 seconds, 700 watts. Step-3. Antibody binding- 100 seconds, 155 watts. Step-4. Conjugate binding- 100 seconds, 155 watts. Step - 5. Color development- 5 minutes at room temperature.
ELISA: Step-1. Ag binding- overnight at 4° C. Step-2. Blocking- 2 h at 37° C. Step-3. Antibody binding- 2 h at 37° C. Step-4. Conjugate binding- 2 h at 37° C. Step - 5. Color development- 5 minutes at room temperature.

| Serial No. | + ve sera | | | | − ve sera | | | |
|---|---|---|---|---|---|---|---|---|
| | MELISA | | ELISA | | MELISA | | ELISA | |
| 1 | 0.567 | 0.556 | 0.539 | 0.560 | 0.036 | 0.070 | 0.046 | 0.040 |
| 2 | 0.531 | 0.556 | 0.538 | 0.534 | 0.096 | 0.056 | 0.064 | 0.070 |
| 3 | 0.541 | 0.563 | 0.549 | 0.547 | 0.098 | 0.053 | 0.064 | 0.050 |
| 4 | 0.558 | 0.545 | 0.574 | 0.544 | 0.052 | 0.080 | 0.074 | 0.110 |
| 5 | 0.557 | 0.564 | 0.558 | 0.540 | 0.049 | 0.079 | 0.056 | 0.090 |
| Remarks | Reproducible | | Reproducible | | Reproducible | | Reproducible | |

TABLE 8

Detection of *Aspergillus fumigatus* antibodies: Comparison of MELISA and ELISA procedures. Same procedures are followed as described in Table-7.

| Sample No. | + ve sera | | | | − ve sera | | | |
|---|---|---|---|---|---|---|---|---|
| | MELISA | | ELISA | | MELISA | | ELISA | |
| 1 | 0.334 | 0.356 | 0.339 | 0.320 | 0.036 | 0.070 | 0.116 | 0.130 |
| 2 | 0.331 | 0.356 | 0.438 | 0.380 | 0.096 | 0.056 | 0.094 | 0.110 |
| 3 | 0.351 | 0.380 | 0.379 | 0.410 | 0.098 | 0.053 | 0.164 | 0.150 |
| 4 | 0.498 | 0.525 | 0.574 | 0.520 | 0.052 | 0.080 | 0.174 | 0.170 |
| 5 | 0.685 | 0.664 | 0.658 | 0.641 | 0.049 | 0.079 | 0.056 | 0.080 |
| 6 | 0.367 | 0.375 | 0.372 | 0.390 | 0.063 | 0.047 | 0.093 | 0.110 |
| 7 | 0.430 | 0.449 | 0.412 | 0.400 | 0.114 | 0.131 | 0.110 | 0.150 |
| 8 | 0.550 | 0.560 | 0.527 | 0.510 | 0.090 | 0.077 | 0.098 | 0.100 |
| 9 | 2.204 | 2.081 | 1.984 | 2.300 | 0.058 | 0.061 | 0.073 | 0.120 |
| 10 | 0.346 | 0.341 | 0.327 | 0.310 | 0.039 | 0.037 | 0.142 | 0.160 |
| Remarks | Comparable | | | | Less non specific binding in MELISA | | | |

Apparatus for MELISA

The apparatus for MELISA can be constructed with the following components:

(a) Loading chamber: It is the chamber for loading the samples or reagents from a specified bottle through a fine tube and a suitable pump onto the activated polystyrene plate/module automatically.

(b) Reaction chamber: Reaction chamber is consisting of magnetron, exhaust fan and a light focus for carrying out the steps of binding of the antigen, blocking, antibody binding and antibody enzyme conjugate binding by microwave irradiation and enzyme substrate reaction at ambient temperature in a pre-programmed time as claimed in claim 1.

(c) Washing cum drying chamber: In this chamber washing and drying of the ELISA plate or module is done automatically by a pre-programmed command after each step of the MELISA procedure;

(d) Detection chamber: This chamber is used for colorimetric detection with the help of the spectrophotometer;

(e) Moving platform: It is used for carrying the Elisa plate/modules from one chamber to chamber;

(f) Control unit: It has microprocessor based computing means for controlling MELISA method as claimed in claim 1 through suitable hardware and software.

ADVANTAGES OF THE INVENTION

Conventional methods of ELISA usually take several hours to 2 days for completion, which is the major drawback for a procedure used worldwide in different fields apart from clinical diagnostics. In case of medical urgency precious time is lost in diagnosis before the patient could be given medication. Therefore, a rapid ELISA procedure invented herein (MELISA) will be beneficial and useful for diagnosis of diseases, biomedical research and other related fields. The main advantages of the invented ELISA procedure are:

1. The invented procedure is very fast than the existing methods of ELISA.
2. The total time required in the invented method is less than 10 minutes. Thus it obviates the time consuming cumbersome procedure.
3. The invented procedure is very sensitive and requires minute quantities of precious antigen or antibody.
4. The invented procedure is very accurate as the enzyme-substrate reaction is done in solution and quantified spectrophotometrically.
5. The procedure is simple and does not require any additional expertise or reagent to do it.
6. The invented procedure is cost effective and does not require any additional equipment except a domestic microwave oven, which is common in most of the laboratories.
7. The invented procedure is reproducible which is an important criterion for ELISA.
8. The procedure gives minimal or negligible non-specific binding.
9. The procedure has the potential for automation, which can minimize human error, which usually varies from person to person.
10. The invented procedure has the potential for application in other immunoassays like radio immunoassay, radio-immunosorbent test, radio allergosorbent test, biotin-avidin/streptavidin immunoassay, immnunoblotting, immunostaining etc. apart from different types of ELISA such as direct ELISA, indirect ELISA, sandwich ELISA and alike.

Thus the invented ELISA procedure which is rapid, economical, reproducible, simple and has a potential for automation. It will be beneficial to human kind due to its increasing importance in clinical diagnostics, molecular biology, agriculture, food technology, environmental science, biomedical research and other related fields

REFERENCES

1. Douillard, J. Y. and Hoffman, T. (1983) *Methods in Enzymology* 92, 168–174.
2. Van Emon, J. M. and Lopez-Avila, V. (1992) *Analytical Chemistry*, 64. 79 A-88A.
3. Linde, D. G. and Goh, K. S.(1995) *Pesticide Outlook*, 18–23
4. Salgame, P., Varadhachary, A. S, Primiano, L. L., Finke, J. E., Muller, S. and Monestier, M. (1996) *Nucleic Acids Res.* 25, 680–681.
5. Satoh, A., Fukui S., Yoshino, S. Shinoda, M., Kozima, K. and Matsumoto, I. (1999) *Analytical Biochemistry* 275, 231–235.
6. Larsson, P. H., Johansson, S. G. O., Hult, A. and Gothe, S. (1987) *Journal of Immunological Methods* 98, 129–135.
7. Boon, M. E and Kok, L. K. (1992) Microwave irradiation in immunostaining, p. 256–285. In Microwave Cookbook of Pathology: The Art of Microscopic Visualisation. 3$^{rd}$. Ed. Columbia press Leyden, Leiden.
8. Boon, M. E., Kok, L. K., Moorlag, H. E. and Suurmeijer (1989). Am.J.Clin. Pathol. 92:137–143.
9. Chiu, K. Y. and K. W. Chan. 1987. J.Clin.Pathol. 40:689–692.
10. Hjerpe, A., Boon, M. E. and Kok, L. P. (1988). Histochem.J. 20:388–396.
11. Koh, L. P. and Boon, M. E. (1992) Microwave Cookbook for Microscopists: Art and Science of Visualization, Third Edition. Coulomb Press Leyden: The Netherlands
12. Sawhney, S., Chakravarti, R. N., Jain, P. and Vinayak, V. K. 1980, Trans.Roy.Soc.Trop.Med.Hyg. 74: 26–29
13. Sharma, G. L, Naik, S. R. and Vinayak, V. K. 1984, Aust.J.Exp.Biol.Med.Sc. 62: 117–133.
14. Lowry, O. H., Rosebrough, N. J., Farr, A. L. and Randall, R. J. 1951, J.Biol.Chem. 193:265.
15. Voller A., Bidwell D, Bartett A. Microplate ELISA and its application, In Immunoenzymatic Assay Techniques. Malvano R. ed. The Hague Martinus Nijhoff Publ. 1980, p 104–115.
16. Banerjee, B., Chetty, A., Joshi, A. P., and Sarma, P. U., 1990, *Asian Pacific J Allergy immunol* 8:13–18).
17. Rosenberg, M., Patterson, R., Mintzer, R., Cooper, B. J., Roberts, M. and Harris, K. E., *Ann Intern Med* 1997, 86:405–414).

OTHER REFERENCES

Patent Documents

April, 1989 Boon et al PCT patent application WO 89/03038

We claim:

1. A rapid method for microwave mediated enzyme-linked immunosorbent assay (MELISA) comprising the steps of:

a) providing a support in one or more wells to provide one or more activated wells;

b) loading a biomolecule selected from an antigen or antibody into the one or more activated wells and binding the biomolecule to the one or more activated wells by irradiating with microwaves at a frequencyrangingbetween 2300–2500 MHz with the power output ranging between 600–900 Watts for 50–100 seconds followed by washing with a washing buffer to immobilize the biomolecule;

c) blocking free surfaces of the one or more activated wells by loading a blocking solution and irradiating with microwaves at a frequency of from 2300–2500 MHz with a power output ranging between 600–800 Watts for 5–20 seconds and washing with a washing buffer;

d) binding a second antibody or antigen to the immobilized biomolecule by irradiating with microwaves at a frequency of from 2300–2500 MHz with a power output ranging from 50–200 Watts for 90–200 seconds followed by washing with a washing buffer;

e) binding an enzyme-conjugate to the immobilized biomolecule having a bound corresponding antibody or antigen by irradiating with microwaves at a frequency of from 2300–2500 MHz with a power output ranging from 100–300 watts for 50–150 seconds followed by washing with a washing buffer to form a product; and f) adding a substrate-dye-buffer to the product before storing for 4 to 10 minutes in dark followed by adding a stop solution before measuring the optical density of the product.

2. A method as claimed in claim 1 wherein the support is selected from the group consisting of polystyrene, polypropylene, glass, cellulose, nitrocellulose, silicagel, polyvinyl chloride, polyaniline and mixtures thereof.

3. A method as claimed in claim 2 wherein the support is polystyrene.

4. A method as claimed in claim 1 wherein the support is in the form of sheets, plates, test particles, test tubes, test sticks, test strips, well, ELISA plate, or microwell plate.

5. A method as claimed in claim 4 wherein the test particles are beads or microspheres.

6. A method as claimed in claim 1 wherein the support has at least one active functional group selected from the group consisting of halide, aldehyde, acetyl, epoxide, succinamide, isothiocyanate, acylazide and mixtures thereof.

7. A method as claimed in claim 6 wherein the at least one active functional group is a part of the support itself or introduced by chemical or photochemical methods.

8. A method as claimed in claim 1 wherein the antigen elicits an immune response.

9. A method as claimed in claim 1 wherein the blocking solution is selected from the group consisting of bovine serum, albumin, skimmed milk powder, gelatin and mixtures thereof.

10. A method as claimed in claim 1 wherein the washing buffer is a mixture of phosphate buffer saline and Tween 20 (polyoxyethylene 20 sorbitron monolaurate), wherein the Tween 20 (polyoxyethylene 20 sorbitron monolaurate) is in the range of 0.05% to 3%.

11. A method as claimed in claim 10 wherein the phosphate buffer saline has a pH in the range of 6.5 to 11 with a molarity ranging from 0.005 to 0.1 M.

12. A method as claimed in claim 1 wherein the enzyme conjugate has an enzyme selected from peroxidase or alkaline phosphate and the conjugate is selected from a biomolecule having an antigen or antibody.

13. A method as claimed in claim 1 wherein the method is useful for assays selected from the group consisting of radio immunoassay, radio-immunosorbent test, radio allergosorbent test, biotin-avidin/streptavidin immunoassay, immunoblotting, immunostainning, different types of ELISA, and mixtures thereof.

14. A method as claimed in claim 13 wherein the different types of ELISA are selected from direct ELISA, indirect ELISA, and sandwich ELISA.

* * * * *